(12) United States Patent
Zhang

(10) Patent No.: US 7,626,696 B2
(45) Date of Patent: Dec. 1, 2009

(54) METHOD AND APPARATUS FOR RECONFIGURABLE FIELD OF VIEW IN A FAST-BASED IMAGING SYSTEM

(75) Inventor: Jingyun Zhang, Upper St. Clair, PA (US)

(73) Assignee: ChemImage Corporation, Pittsburgh, PA (US)

( * ) Notice: Subject to any disclaimer, the term of this patent is extended or adjusted under 35 U.S.C. 154(b) by 106 days.

(21) Appl. No.: 11/890,517

(22) Filed: Aug. 7, 2007

(65) Prior Publication Data

US 2009/0040519 A1 Feb. 12, 2009

(51) Int. Cl.
*G01J 3/02* (2006.01)
*G01J 3/28* (2006.01)
*G01N 21/64* (2006.01)
*G01N 21/65* (2006.01)

(52) U.S. Cl. ............... 356/326; 356/301; 356/317; 385/116; 385/121

(58) Field of Classification Search ............ 356/301, 356/326, 328; 385/116, 121
See application file for complete search history.

(56) References Cited

U.S. PATENT DOCUMENTS

| | | | |
|---|---|---|---|
| 3,984,190 A | 10/1976 | Barrett et al. | |
| 4,195,931 A | 4/1980 | Hara | |
| 4,200,801 A | 4/1980 | Schuresko | |
| 4,487,504 A * | 12/1984 | Goldsmith | 356/323 |
| 4,553,816 A | 11/1985 | Durand et al. | |
| 4,660,151 A | 4/1987 | Chapman et al. | |
| 4,701,838 A | 10/1987 | Swinkels et al. | |

(Continued)

FOREIGN PATENT DOCUMENTS

WO 0177648 A1 10/2001

(Continued)

OTHER PUBLICATIONS

Conti, S., et al., "Traces of Polymethylsiloxane in case histories of rape: technique for detection," Elsvier Science Ireland Ltd, Forensic Science International, Jan. 1995, pp. 121-128.

(Continued)

*Primary Examiner*—F. L Evans
(74) *Attorney, Agent, or Firm*—Duane Morris LLP

(57) ABSTRACT

A system and method to obtain a variable field of view (FOV) of a sample without requiring an increase in an imaging CCD array size. In a fiber array spectral translator (FAST) based chemical imaging system, the fibers in the fiber bundle may be organized in different 2D "zones". Each zone may include a predetermined number of fibers. Each 2D zone of fibers at the signal input end is organized as a separate linear array (1D) at the spectrometer slit input end. Depending on the user-selected FOV, one or more zones of fibers may be selected for signal input (into the spectrometer) by a motorized mobile slit port or linear translating stage, which will sequentially scan output from each selected linear fiber array into the spectrometer slit. The user can switch from one FOV size to another, thereby activating the linear translating stage to gather signals from appropriate linear fiber arrays corresponding to fiber zones associated with the selected FOV. A CCD imager may be used to collect optical data and generate 2D spatially accurate wavelength resolved images of the user-selected FOV.

51 Claims, 9 Drawing Sheets

U.S. PATENT DOCUMENTS

| | | | |
|---|---|---|---|
| 4,766,551 | A | 8/1988 | Begley |
| 4,885,697 | A | 12/1989 | Hubner |
| 5,072,338 | A | 12/1991 | Hug et al. |
| 5,121,337 | A | 6/1992 | Brown |
| 5,121,338 | A | 6/1992 | Lodder |
| 5,124,932 | A | 6/1992 | Lodder |
| 5,311,445 | A | 5/1994 | White |
| 5,324,567 | A | 6/1994 | Bratchley et al. |
| 5,347,378 | A | 9/1994 | Handschy et al. |
| 5,357,340 | A | 10/1994 | Zochbauer |
| 5,481,476 | A | 1/1996 | Windig |
| 5,606,164 | A | 2/1997 | Price et al. |
| 5,610,836 | A | 3/1997 | Alsmeyer et al. |
| 5,710,713 | A | 1/1998 | Wright et al. |
| 5,751,415 | A | 5/1998 | Smith et al. |
| 5,801,828 | A | 9/1998 | Collins |
| 5,822,219 | A | 10/1998 | Chen et al. |
| 5,866,430 | A | 2/1999 | Grow |
| 6,002,476 | A | 12/1999 | Treado |
| 6,008,888 | A | 12/1999 | Nottke et al. |
| 6,239,904 | B1 | 5/2001 | Serfling et al. |
| 6,485,981 | B1 | 11/2002 | Fernandez |
| 6,549,861 | B1 | 4/2003 | Mark et al. |
| 6,584,413 | B1 | 6/2003 | Keenan et al. |
| 6,614,532 | B1 | 9/2003 | Power et al. |
| 6,621,614 | B1 | 9/2003 | Zhang |
| 6,631,001 | B2 | 10/2003 | Kuisevo |
| 6,833,957 | B2 | 12/2004 | Sato |
| 6,836,366 | B1 | 12/2004 | Flanders et al. |
| 6,897,951 | B2 | 5/2005 | Womble et al. |
| 6,970,246 | B2 | 11/2005 | Hansen et al. |
| 6,985,216 | B2 | 1/2006 | Treado et al. |
| 6,985,233 | B2 | 1/2006 | Tuschel et al. |
| 7,012,695 | B2 | 3/2006 | Maier et al. |
| 7,072,770 | B1 | 7/2006 | Schweitzer et al. |
| 7,084,972 | B2 | 8/2006 | Treado |
| 2006/0209301 | A1 | 9/2006 | Gardner, Jr. et al. |

FOREIGN PATENT DOCUMENTS

| | | |
|---|---|---|
| WO | 2007/101279 | 9/2007 |

OTHER PUBLICATIONS

Lee, G.S.H., et al., "A Methodology Based on NMR Spectroscopy for the Forensic Analysis of Condoms," St. Andrews Centre for Advanced Materials, pp. 808-821, Journal of Forensic Sciences, 2001.

Maynard, P., et al., "A protocol for the forensic analysis of condom and personal lubricants found in sexual assault cases," Forensic Science International, 124 (2001), pp. 140-156.

Stoilovic, M., et al., "The Application of Light in Forensic Science & A Modern Approach to Fingerprint Detection and Enhancement," Australian Federal Police, AFP Workshop Manual, Oct. 2000.

Roux, C., et al., "Evaluation of 1,2-Indanedione and 5,6-Dimethoxy-1,2-Indanedione for the Detection of Latent Fingerprints on Porous Surfaces," Journal of Forensic Sciences, vol. 45(4), 2000, pp. 761-769.

Roux, C., et al., "A study to investigate the evidential value of blue and black ballpoint pen inks in Australia," Forensic Science International, 101 (1999), pp. 167-176.

Mazzella, W.D., et al., "Classification and Identification of Photocopying Toners by Diffuse Reflectance Infrared Fourier Transform Spectroscopy (DRIFTS): I. Preliminary Results," Journal of Forensic Sciences, JFSCA, vol. 36, No. 2, Mar. 1991, pp. 449-465.

Mazzella, W.D., et al., "Classification and Identification of Photocopying Toners by Diffuse Reflectance Infrared Fourier Transform Spectroscopy (DRIFTS): II. Final Report," Journal of Forensic Sciences, JFSCA, vol. 36, No. 3, May 1991, pp. 820-837.

Brunelle, R.L., "Questioned Document Examination," Bureau of Alcohol, Tobacco, and Firearms, U.S. Treasury Department, 1982.

Robertson, J., et al., "The Persistence of Textile Fibres Transferred During Simulated Contacts," Journal of Forensic Sciences, vol. 22, No. 4, Oct. 1982, p. 353-360.

Gaudette, B.D., "The Forensic Aspects of Textile Fiber Examination," Central Forensic Laboratory, Royal Canadian Mounted Police.

Pounds, C.A., et al., "The Transfer of Fibres between Clothing Materials During Simulated Contacts and their Persistence During Wear: Part I—Fibre Transference," Journal of Forensic Sciences, vol. 15, 1975, pp. 17-27.

Pounds, C.A., et al., "The Transfer of Fibres between Clothing Materials During Simulated Contacts and their Persistence During Wear: Part II—Fibre Persistence," Journal of Forensic Sciences, vol. 15, 1975, pp. 29-37.

Maynard, P., et al., "Adhesive Tape Analysis: Establishing the Evidential Value of Specific Techniques," Journal of Forensic Sciences, vol. 46(2), 2001, pp. 280-287.

Caetano, M.R., et al., "Evaluation of the importance of non-linear spectral mixing in coniferous forests," EUROPTO Conference on Remote Sensing for Agriculture, Ecosystems, and Hydrology, Barcelona, Spain, Sep. 1998.

Rasmussen, G.T., et al., "Library Retrieval of Infrared Spectra Based on Detailed Intensity Information," Applied Spectroscopy, vol. 33, No. 4, 1979.

Guilment, J., et al., "Infrared Chemical Micro-Imaging Assisted by Interactive Self-Modeling Multivariate Analysis," Applied Spectroscopy, vol. 48, No. 3, 1994.

Engman, E.T., "Remote Sensing for Agriculture, Ecosystems, and Hydrology," Proceedings of SPIE EUROPTO Series, vol. 3499, Sep. 22-24, 1998.

Press, W.H., et al., Numerical Recipes in C, The Art of Scientific Computing, 2nd ed., Cambridge, NY: Cambridge University Press, 1992.

Malinowski, E.R., Factor Analysis in Chemistry, 2nd ed., New York, NY: John Wiley & Sons, Inc., 1991.

* cited by examiner

METHOD AND APPARATUS FOR RECONFIGURABLE FIELD OF VIEW IN A FAST-BASED IMAGING SYSTEM

BACKGROUND

Chemical imaging has a powerful capability for material characterization, process monitoring, quality control and disease-state determination. Chemical imaging combines chemical analysis with high-resolution optical imaging including optical spectroscopy, Raman imaging as well as fluorescent and IR techniques.

Raman effect is a phenomenon in which a specimen scatters incident light of a given frequency into a spectrum which has lines caused by interaction of the incident light with the molecules making up the specimen. Different molecular species have different characteristic Raman spectra. Consequently, the Raman effect can be used to analyze the molecular species present in the sample. Raman chemical imaging provides molecular-specific image contrast without the use of stains or dies. Raman image contrast arises from a material's intrinsic vibrational spectroscopic signature which is highly sensitive to the composition and structure of the sample as well as its local environment. As a result, Raman imaging can be performed with little or no sample preparation and is widely applicable for material research, failure analysis, process monitoring and clinical diagnosis.

Compared to conventional non-imaging systems, a chemical imaging system based on a tunable filter enables visualizing the distribution (morphology and architecture) of chemical species in heterogeneous samples with molecular compositional specificity. Raman images can be collected non-invasively with limited or no sample preparation, at high spatial resolution, and with high fidelity where the spatial fidelity is limited by the number of pixels of a charge coupled device (CCD) detector. Most importantly, every image pixel has associated with it a Raman spectrum whose quality is comparable to that obtained with conventional non-imaging spectrometers. Chemical imaging simultaneously provides image information on the size, shape and distribution (the image morphology) of molecular chemical species present within the sample.

In order to acquire 3D data sets in Raman imaging systems, the two dimensions of the image are recorded directly by a CCD camera while the multispectral information is acquired by capturing images at discrete wavelengths selected by the tunable filter, e.g., a liquid crystal tunable filter or LCTF.

In general, LCTF is an electro-optically controllable spectral bandpass filter which can function from the visible region to the near IR with a continuously tunable wavelength. In an imaging system, an LCTF is free of image shift with tuning. However, LCTFs have noticeable drawbacks. For example, LCTFs have a low peak transmittance. In addition, LCTFs are susceptible to thermally-induced drift in their spectral bandpass. In theory, the LCTF is free of optical distortions and spectral leakage; but in reality these defects always exist. Finally, LCTF systems are costly. Therefore, it is desirable to address the signal loss (and, hence, loss of efficiency) issues associated with LCTFs.

SUMMARY

In one embodiment, the disclosure relates to an LCTF-less chemical imaging system with reconfigurable field of view (FOV). The system comprising a first optical transmitter for converting a first 2D optical dataset collected from a first 2D portion of a sample to a first 1D optical dataset; a second optical transmitter for converting a second 2D optical dataset collected from a second 2D portion of the sample to a second 1D optical dataset; and a switching mechanism for selectively communicating one of the first 1D optical dataset or the second 1D optical dataset to a spectrometer.

A method disclosed comprises converting a first 2D optical dataset depicting a first portion of a sample to a first 1D optical dataset, converting a second 2D optical dataset depicting a second portion of the sample to a second 1D optical dataset; and selectively communicating the first and the second 1D optical datasets to a spectrometer to obtain spectral data for the sample.

An additional embodiment described is a system comprising a switching mechanism having an input for receiving a plurality of 1D optical datasets from a plurality of optical fiber bundles; and a processor in communication with the switching mechanism and programmed with instructions for controlling the switching mechanism to select a first 1D optical dataset from one of the plurality of optical fiber bundles, to communicate the first 1D optical dataset to a spectrometer, to select a second 1D optical dataset from another of the plurality of optical fiber bundles, and to communicate the second optical 1D dataset to the spectrometer.

A further embodiment is disclosed in which a fiber bundle comprises an optical signal input end formed by a plurality of optical fibers organized in a plurality of non-overlapping 2D zones, wherein each zone includes a predetermined number of fibers; and an optical signal output end formed by a plurality of zone-specific curvilinear arrays of optical fibers in the plurality of optical fibers, wherein each curvilinear array contains a 1D arrangement of a corresponding set of zone-specific fibers from the plurality of fibers.

BRIEF DESCRIPTION OF THE DRAWINGS

These and other embodiments of the disclosure will be discussed in relation to the following non-limiting and exemplary drawings, in which.

DETAILED DESCRIPTION

Figure 1:
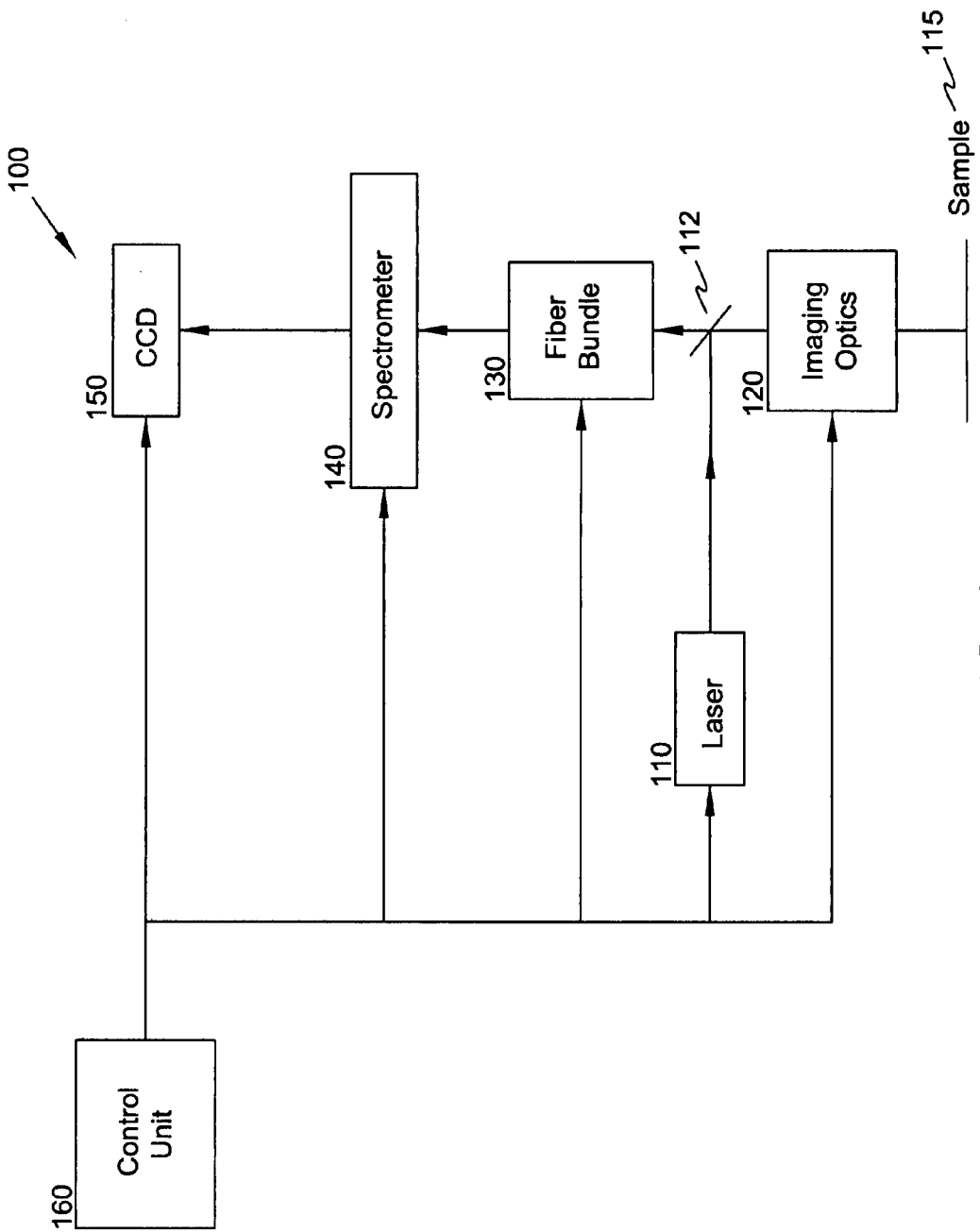
FIG. 1 is a schematic representation of a prior art chemical imaging system.

FIG. 1 is a schematic representation of a prior art chemical imaging system 100. In FIG. 1, sample 115 is illuminated by laser illumination source 110. The illuminating photons are transmitted through mirror 112 and through imaging optics 120. Mirror 112 can be a dichroic mirror. Imaging optics 120 can comprise an optical train including one or more lenses (not shown) and other optical elements (not shown). The photons received from the sample 115 (e.g., through reflection, scattering, etc.) are collected by imaging optics 120 and are directed to an optical fiber bundle 130. Arrangement of the optical fiber bundle will be described in greater detail below in conjunction with discussion of FIGS. 2 and 3. Control unit 160 communicates with laser source 110, imaging optics 120, fiber bundle 130, spectrometer 140, CCD 150 and optionally, mirror 112. Control unit 160 can integrate and control the operation of system 100.

The optical fiber bundle 130 communicates an optical dataset to spectrometer 140 to form spectra. Spectrometer 140 can define a spectrograph. Optionally, the spectra from gratings (not shown) in the spectrometer 140 can be communicated to the Charge-Coupled Device (CCD) 150 to form an image of sample 115. The image can define a spatially accurate wavelength-resolved image of the sample. A spatially accurate wavelength-resolved image is an image of a sample that is formed from multiple "frames" wherein each frame has plural spatial dimensions and is created from photons of a particular wavelength (or wave number) or from photons in a particular wavelength band (or wave number band) so that the frames may be combined to form a complete image across all wavelengths (wave numbers) of interest.

Figure 2:
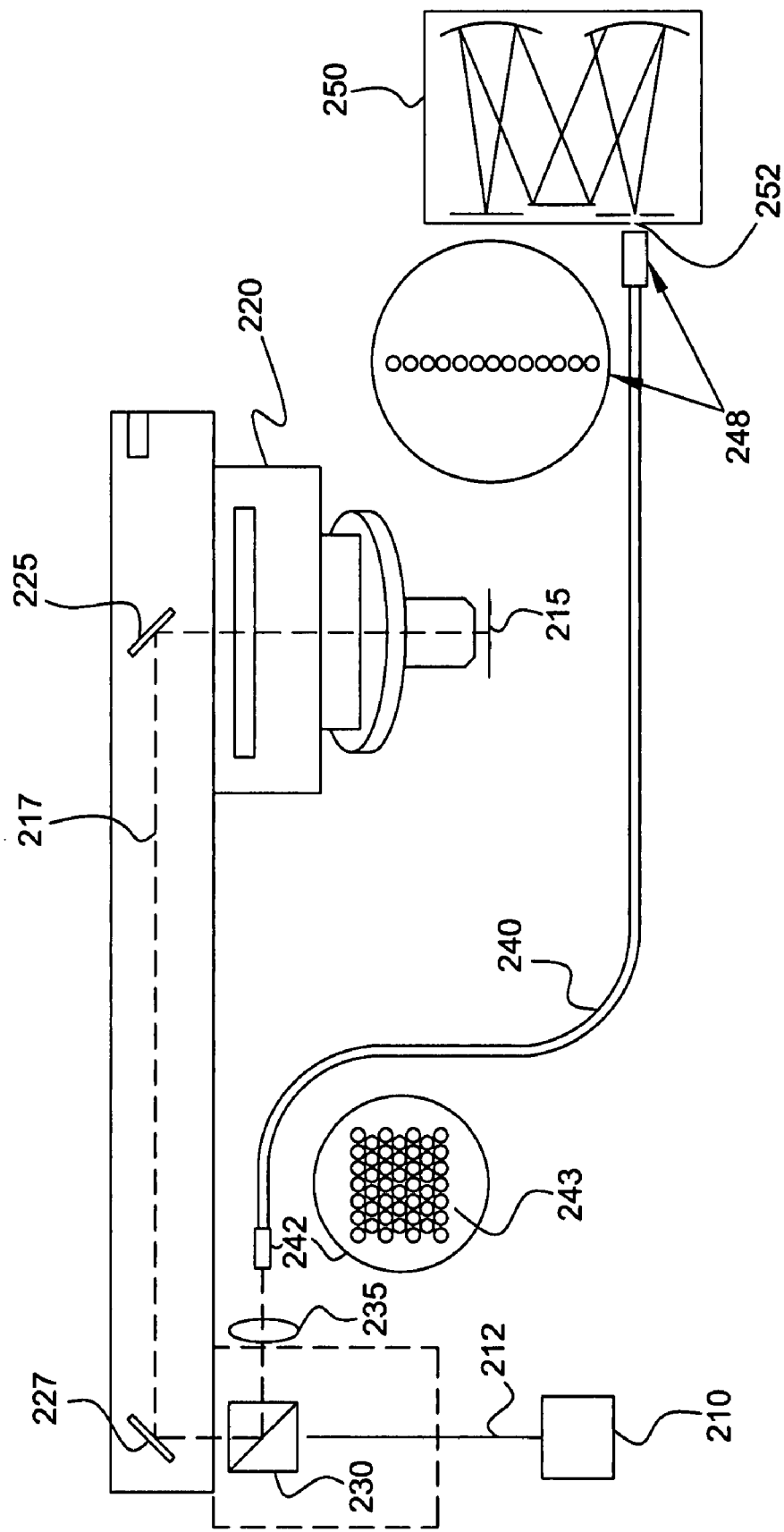
FIG. 2 shows a prior art FAST based system for implementing the representation of FIG. 1.

FIG. 2 shows a prior art FAST (Fiber Array Spectral Translator) based system for implementing the representation of FIG. 1. In FIG. 2, illumination source 210 provides illuminating photons 212 to sample 215 through optical beam splitter 230, mirrors 227 and 225, and optical train 220. After illumination, sample photons 217 received from the sample 215 are collected by optical train 220 and directed through mirrors 225 and 227, optical splitter 230 and objective lens 235 to input port 242 of an optical fiber bundle 240. Objective lens 235 focuses sample photons 217 to an image plane 243 of input port 242. As shown in FIG. 2, image plane 243 can comprise a two dimensional (2D) input surface of optical fiber bundle 240.

Port 248 defines the output end of optical fiber bundle 240. Optical fibers are substantially linearly arranged at output port 248. While not specifically shown in FIG. 2, input port 242 and output port 248 have the same number of optical fibers. The rearrangement of the optical fibers from input port 242 to output port 248 enables conversion or translation of a two-dimensional (2D) optical dataset at input port 242 to a one-dimensional (1D) optical dataset at output port 248. The 1D optical dataset can be communicated with spectrometer opening slit 252. Spectrometer 250 can be a spectrograph.

Figure 3:
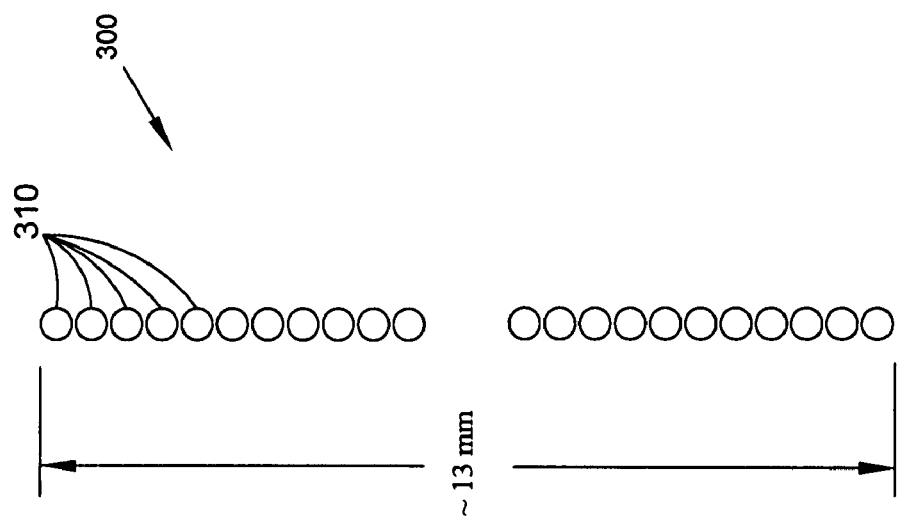
FIG. 3 shows a prior art substantially linear arrangement of fibers in an optical fiber's output port for communication with a spectrometer slit in the system of FIG. 2.

FIG. 3 shows a prior art substantially linear arrangement of fibers in an optical fiber's output port (e.g., the output port 248 in FIG. 2) for communication with a spectrometer slit. A gratings-based spectrometer may have an input slit with a length of about 13.312 mm. This length may be dictated by the number of imaging pixels in a CCD (not shown in FIGS. 2-3) receiving the wavelength dispersed spectra from the spectrometer. Accordingly, output port 300 is shown to have a length of about 13 mm to fit the spectrometer slit. By substantially linearly arranging the fiber array as shown in FIG. 3, substantially all the data received at the input port of the optical fiber can be communicated to the spectrometer. In one embodiment, about 208 optical fibers 310 can be arranged to provide a substantially linear or curvilinear fiber array of about 13 mm height.

Figure 4:
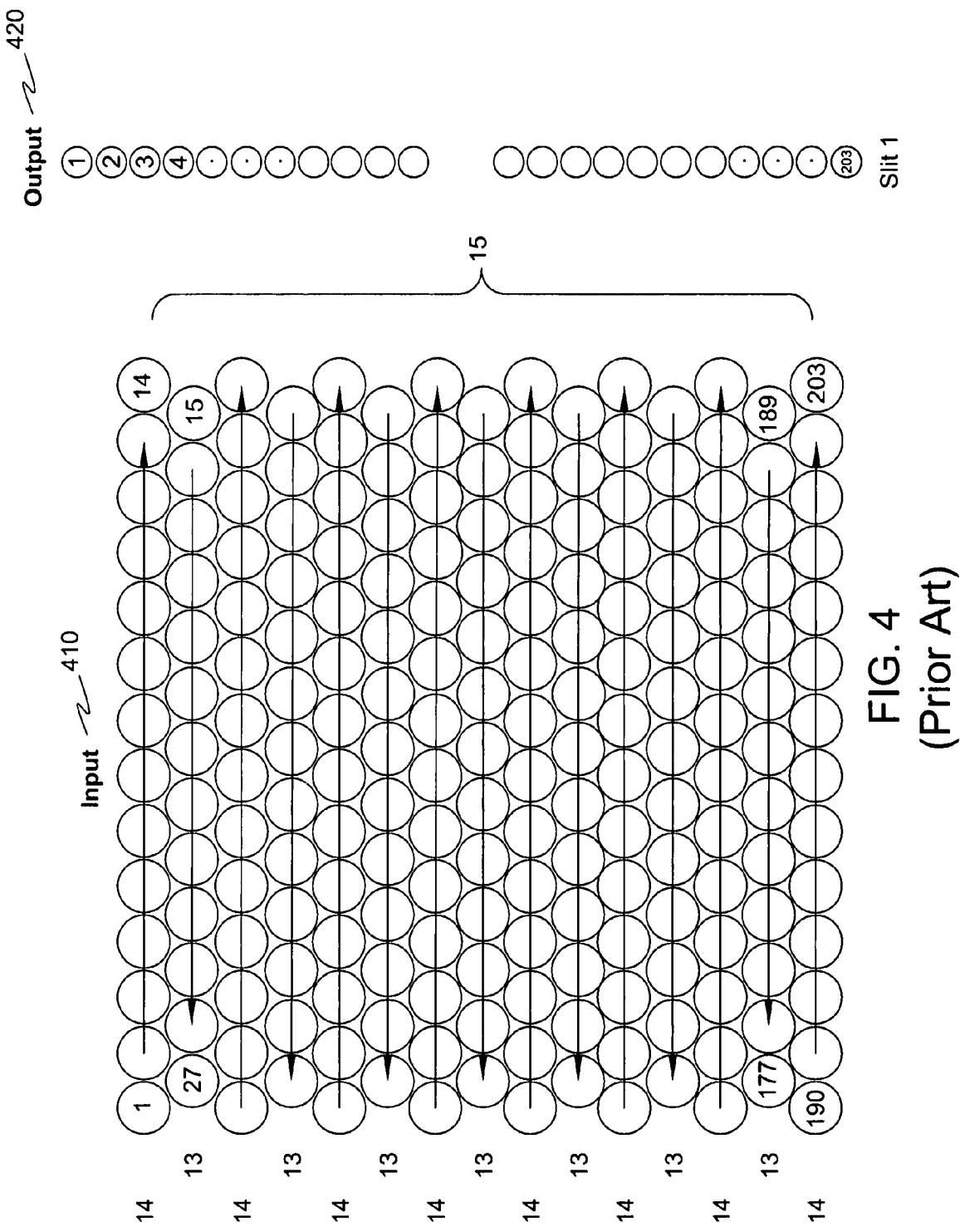
FIG. 4 shows a prior art arrangement of optical fibers at input and output ports of an optical fiber bundle in the system of FIG. 2.

FIG. 4 shows a prior art arrangement of optical fibers at input and output ports of an optical fiber bundle in the system of FIG. 2 (e.g., the fiber bundle 240). On the left hand side of FIG. 4, a total of 203 optical fibers are arranged in a rectangular, two-dimensional format at the input port of the optical fiber bundle. As discussed with reference to FIG. 2, the optical fibers of the input port form a surface for receiving a 2D optical dataset from the sample. The optical dataset can be, for example, an image of the sample or a sub-image depicting a portion of the sample. It is seen in FIG. 4 that the optical fibers in the input port 410 are arranged in a total of 15 rows, wherein each odd-numbered row contains 14 fibers and each even-numbered row contains 13 fibers. There is a total of 8 odd-numbered rows and 7 even-numbered rows in the input port 410, thereby resulting in a total of 203 fibers. On the right hand side, the optical fibers of FIG. 4 are arranged to form a substantially linear array at the output port 420. The linear arrangement enables communicating the optical dataset with a spectrometer slit (not shown) as discussed before. While FIG. 4 shows the optical fibers with a particular numerical arrangement, it should be noted that such arrangement is exemplary and non-limiting.

Figure 6:
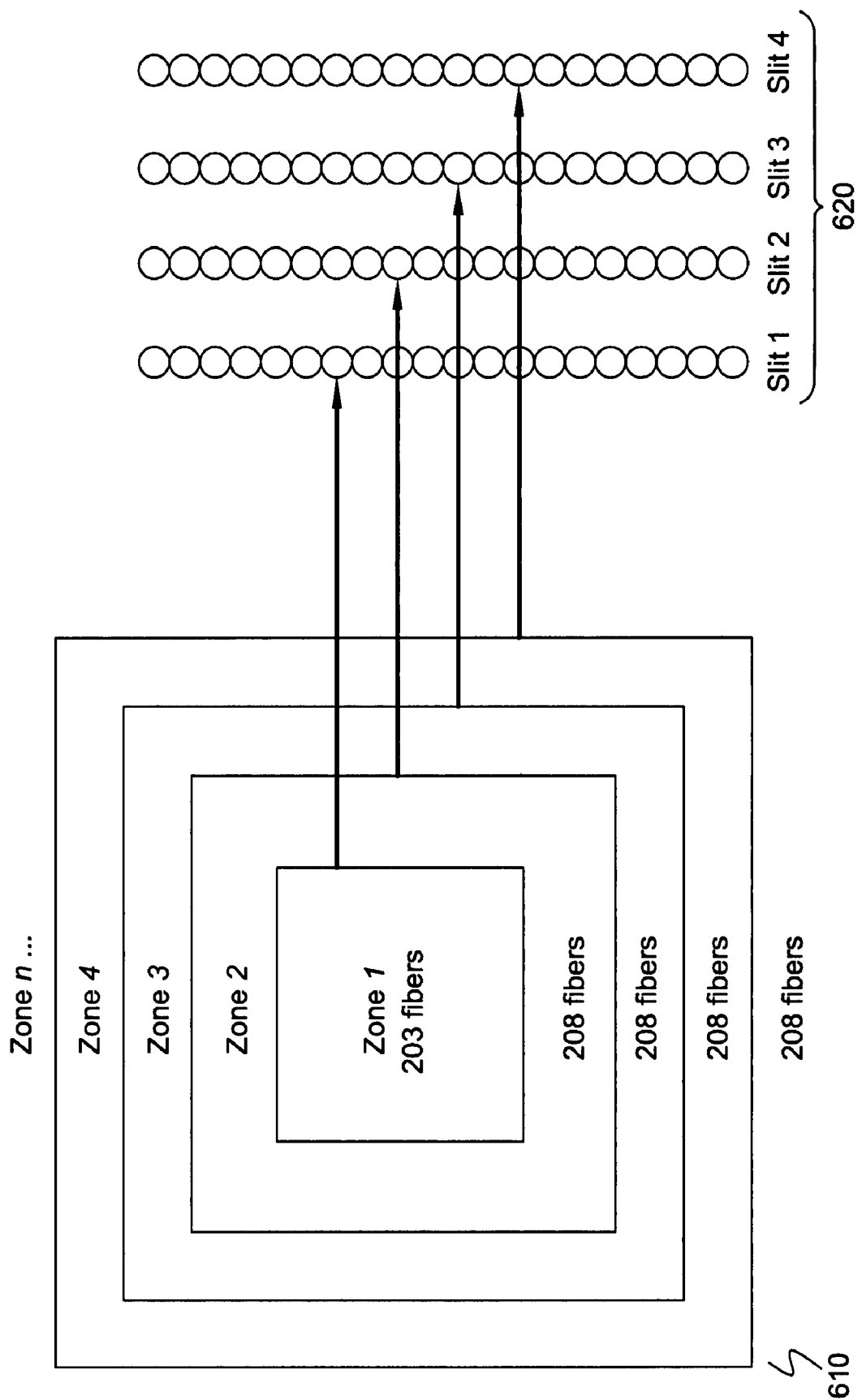
FIG. 6 shows an exemplary arrangement of input and output for several fiber bundles according to one embodiment of the disclosure.

It is seen from the discussion hereinabove that, in a prior art FAST-based chemical imaging system, the size of the 2D fiber bundle at the input end of a FAST fiber will typically dictate the size of the sample's field-of-view (FOV). In order to increase the FOV or to make it variable, the number of fibers in the 2D input end has to be increased. However, because of the 2D to 1D conversion (or spectral "translation") at the spectrometer input slit in a FAST system, an increase in the number of fibers at the input end will require a similar increase in the fibers at the 1D output end, which, in turn, will require a similar increase in the column size of the CCD used to image the light received from the fibers. A larger sized CCD may be expensive, and may not be always practical or desirable. In one embodiment of the present disclosure, this problem is avoided by organizing the FAST fiber bundle in different "zones" of fibers as shown in FIG. 6 and discussed later below.

Figure 5:
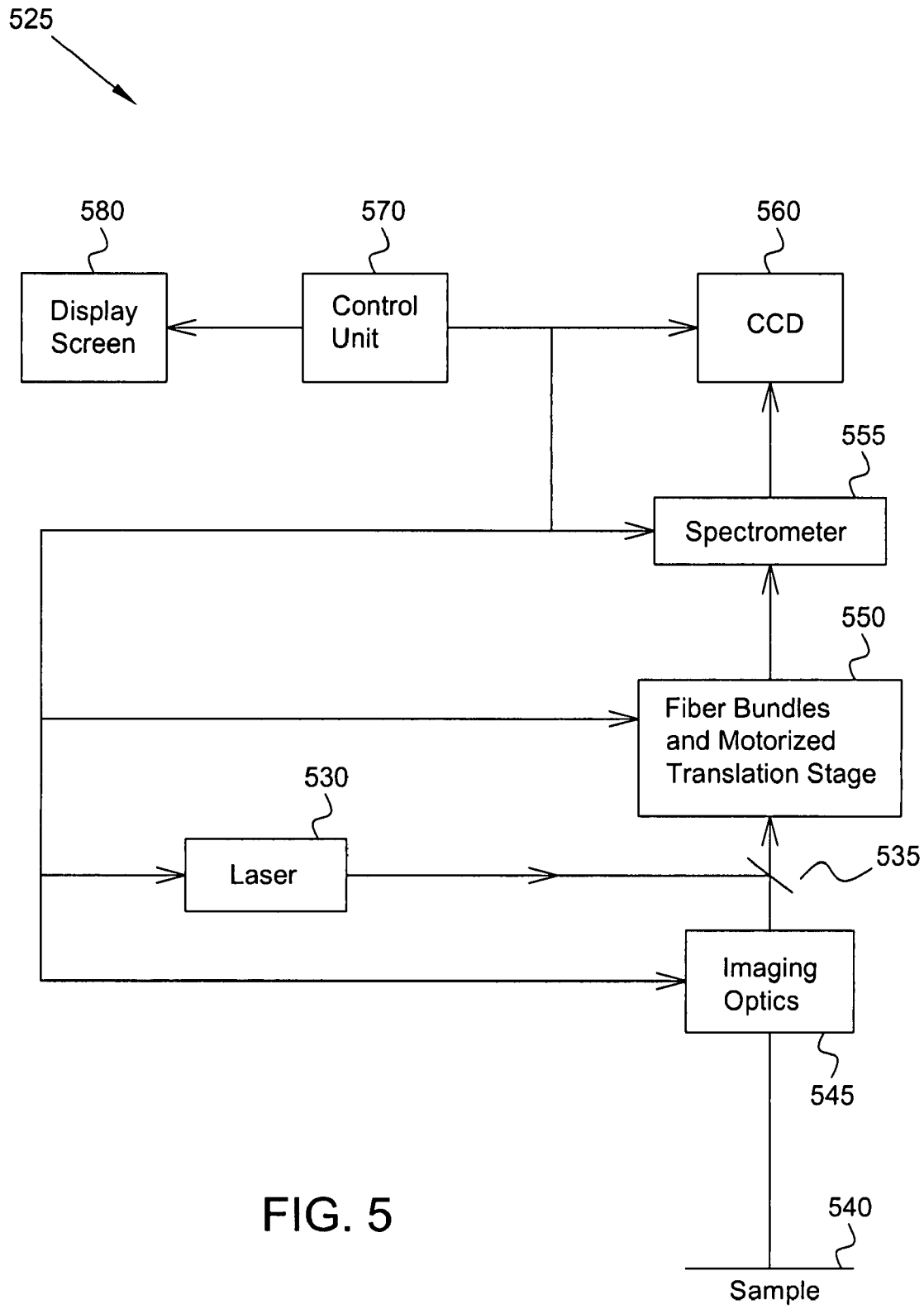
FIG. 5 is a schematic representation of a chemical imaging system according to one embodiment of the present disclosure.
Figure 7:
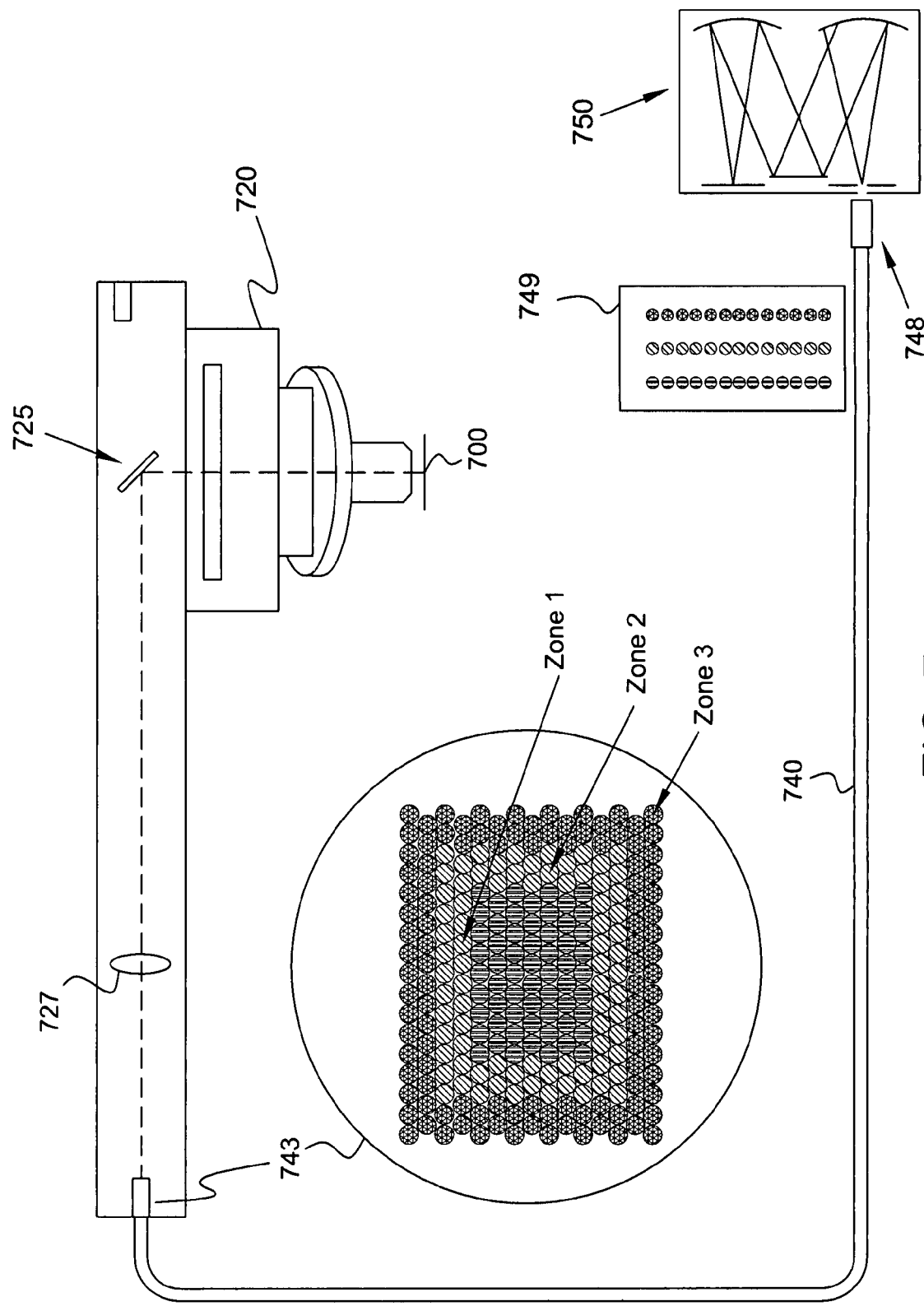
FIG. 7 shows a system according to one embodiment of the disclosure for implementing the arrangement of FIG. 6 in the representation of FIG. 5.

FIG. 5 is a schematic representation of a chemical imaging system 525 according to one embodiment of the present disclosure. The chemical imaging system 525 may be a Raman imaging system, a fluorescence imaging system, or any other type of chemical imaging system employing a fiber bundle for optical signal transmission and a spectrometer operating on a liner input. As in the system of FIG. 1, the system in FIG. 5 relies on 2D to 1D "translation" of input and output fiber arrangements to optically link photons from sample 540 to the spectrometer slit. Various components (e.g., laser 530, spectrometer 555, CCD 560, and mirror 535) in the system 525 in FIG. 5 are functionally similar to the corresponding components in FIG. 1 and, hence, additional discussion of such similar components is not provided herein for the sake of brevity. In one embodiment, the imaging optics 545 may be similar to the imaging optics 120 in FIG. 1. In one embodiment, the imaging optics 545 may be implemented using mirrors, lenses, and optical train based implementation similar to that shown in FIG. 2 and discussed hereinbefore. An alternative arrangement for imaging optics 545 is shown in FIG. 7 and discussed later below. In contrast to the embodiment in FIG. 1, it is shown at block 550 in FIG. 5 that the embodiment in FIG. 5 includes a plurality of fiber bundles or "zones" (discussed below) and a motorized translation stage so as to allow a variable field of view as discussed later hereinbelow. Furthermore, the control unit 570 in FIG. 5 may differ from the control unit 160 in FIG. 1 in that the control unit 570 may be configured to provide special controls for the multiple fiber zones and selection of one or more fiber zones through proper control of the movement of the motorized stage as discussed later below. In one embodiment, the control unit 570 may be a computer processor suitably programmed to carry out fiber bundle selection, motor stage translation, CCD and spectrometer activation, and various other image capture and spectroscopy operations as per the teachings of the present disclosure. In one embodiment, an image (e.g., a Raman image, a fluorescence image, etc.) of the selected FOV may be displayed on a display screen (e.g., a computer display) 580 that is operatively coupled to the control unit 570.

In one embodiment, the CCD 560 may be a CCD camera model MicroMax: 1024B manufactured by Roper Scientific®. In another embodiment, the spectrometer 555 may be the grating-based SpectroPro 500i spectrometer manufactured by Acton Optics (a division of Princeton Instruments).

As noted before, in one embodiment, the disclosure relates to arranging a plurality of fiber bundles in an arrangement adapted to communicate a larger or variable field of view of the sample to the spectrometer. FIG. 6 shows an exemplary arrangement of input 610 and output 620 for several fiber bundles according to one embodiment of the disclosure. In the "zone"-based arrangement of fibers in FIG. 6, each zone may include a predetermined number of fibers. For example, in FIG. 6, zone 1 comprises 203 optical fibers arranged in a square pattern capturing a corresponding field of view of the sample. Zone 2 comprises 208 optical fibers surrounding Zone 1 and capturing a corresponding field of view that surrounds the field of view of Zone 1. Thus, the 208 fibers in Zone 2 are in addition to the 203 fibers in Zone 1, thereby making a total of 411 fibers. Similarly, Zone 3 comprises another 208 fibers and surrounds Zones 1 and 2 capturing a corresponding field of view of the sample which extends beyond Zones 1 and 2. Finally, Zone 4 comprises still additional 208 fibers and surrounds zones 1 through 3. Zone 4 is arranged to capture the field of view not covered by Zones 1 through 3. In the exemplary embodiment of FIG. 6, there is thus a total of 827 fibers in zones 1 through 4. Further, in other embodiments, the number of fibers per zone and the total number of zones at the fiber input port may be different from those illustrated in FIG. 6 and may be flexibly determined depending on the desired size and variability of the sample FOV. Each 2D zone of fibers at the signal input end is organized as a separate curvilinear array (1D) at the spectrometer input end as shown by the four slit arrangements (corresponding to four input fiber Zones 1 through 4) in the output fiber bundle 620. The overall 2D rectangular configuration of the fiber bundles arranged in Zones 1, 2, 3 and 4 defines an input port for a FAST fiber (not shown in FIG. 6, but shown as exemplary fiber 740 in FIG. 7) that may be used in the system of FIG. 5. It should be noted that the rectangular, two-dimensional arrangement of the optical fibers 610 at the input port is exemplary and non-limiting. Indeed, the optical fibers can be arranged to form a circular, hexagonal, polygonal, or any other shape.

FIG. 6 also shows the output of each of Zones 1 through 4 arranged linearly at output 620. The output for each of Zones 1 through 4 is identified, respectively, as Slits 1 through 4. The linear arrangement of the output slits enables direct optical communication from field of views corresponding to Zones 1 through 4 with the spectrometer slit. It is noted here that the fiber outputs are denoted as "Slit 1", "Slit 2", etc., for convenience only and should not be confused with the spectrometer slit. In the embodiment of FIGS. 5 and 7, there is only one spectrometer slit, whereas there may be multiple fiber "slits". As discussed later below, each fiber "slit" or curvilinear (1D) arrangement is brought in optical alignment with the spectrometer slit by the motorized translation stage during operation of a chemical imaging system according to one embodiment of the present disclosure (e.g., the system 450 in FIG. 5). According to one embodiment of the disclosure, an electro-mechanical or an optical switch (not shown) can be used to successively communicate the optical information from each of Slits 1 through 4 to the spectrometer opening.

FIG. 7 shows a system according to one embodiment of the disclosure for implementing the arrangement of FIG. 6 in the representation of FIG. 5. In FIG. 7, photons from sample 700 are collected by the imaging optics 720 and directed through mirror 725 and objective lens 727 to input port 743 of optical fiber bundles. Objective lens 727 (which could be a microlens array to provide more spectral resolution) focuses sample photons onto input port 743 of optical bundle 740. The optical fibers at input port 743 are divided into zones 1, 2 and 3 and each zone captures sample photons corresponding to a different region of the sample's field of view. Thus, optical bundle 740 communicates sample photons from different fields of view of sample 700. It is noted here that the "division" of optical fibers at the input port 743 is more functional than physical. The fibers may still be physically stacked together or all fibers may be part of a single optical fiber cable (e.g., the fiber 740) without physical separation or zoning therebetween. However, when selecting a desired field of view, a system controller (e.g., the control unit 470 in FIG. 5) may "divide" the fibers into "zones" and select signal output from the fibers of the desired zone(s). Output port 748 of optical fiber bundle 740 comprises fiber "slits" 1, 2 and 3 which communicate an optical data set from input fiber zones 1, 2 and 3, respectively, as indicated by the corresponding hatchings for fibers shown in FIG. 7. The 1D fiber ends or "slits" 1, 2 and 3 are shown in the exploded view 749. Each of slits 1, 2 and 3 communicates a one-dimensional optical dataset corresponding to a field of view of each of zones 1, 2 and 3, respectively, to spectrometer 750 (which could be a spectrograph in one embodiment).

In one embodiment, each optical fiber in the fiber bundle 740 may be a multi-mode fiber having a numerical aperture of 0.22. In cross-section, the fiber core may be 50 μm thick, the cladding may be 60 μm thick, and the coating layer may be 64 μm thick. The fiber may have a transmission spectrum from approximately 350 to 2400 nm wavelength range.

Figure 8:
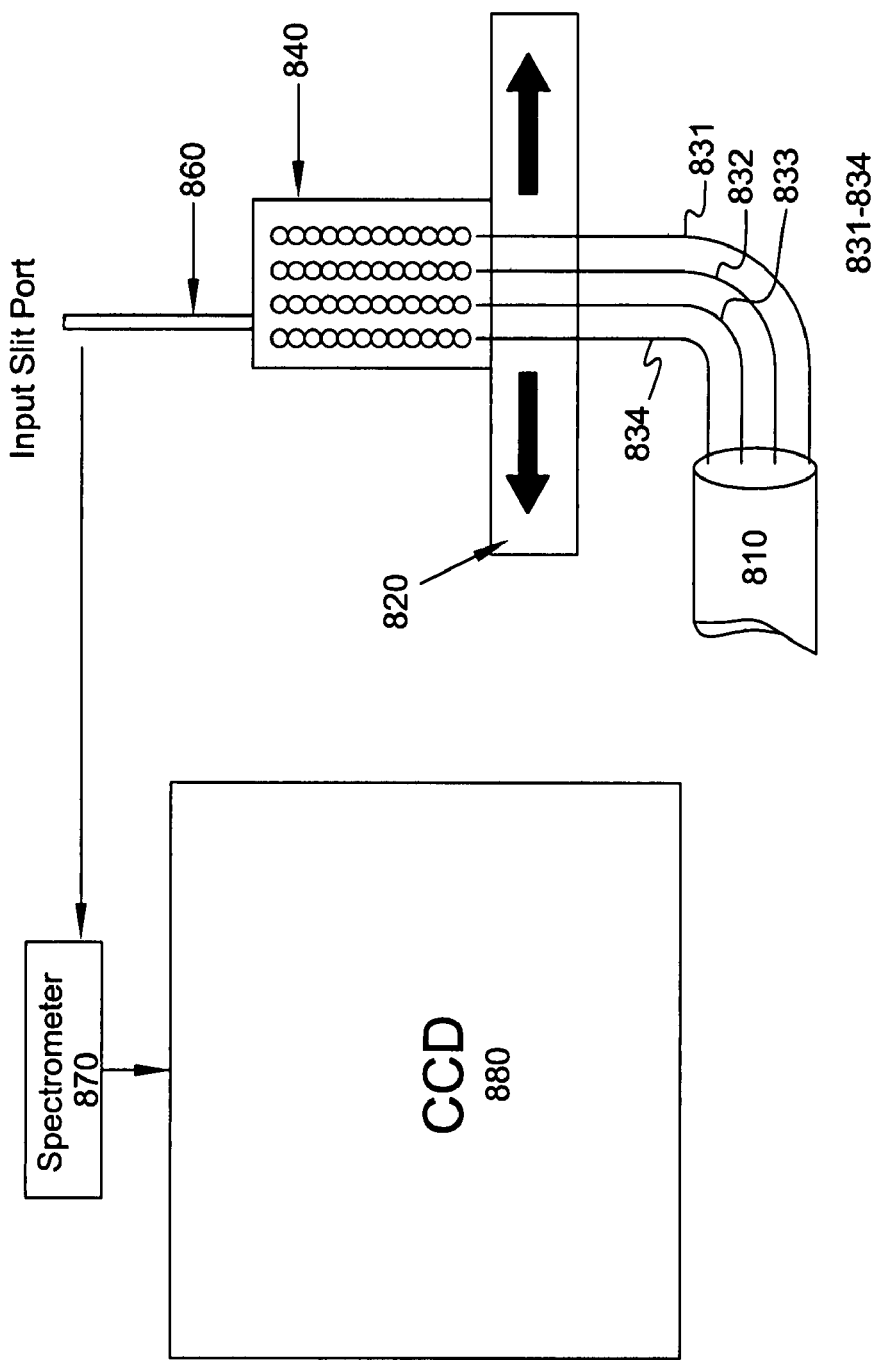
FIG. 8 shows a motorized linear switching system according to one embodiment of the disclosure.

FIG. 8 shows a motorized linear switching system according to one embodiment of the disclosure. More specifically, FIG. 8 shows a motorized linear switching mechanism for selectively communicating one of the one-dimensional optical datasets to a spectrometer slit. In FIG. 8, fiber bundle 810 communicates optical dataset depicting various regions of a sample (not shown). Optical fiber bundle 810 can comprise, for example, four zones where each zone communicates an optical data set from a region of the sample (not shown). Each of the four zones of the optical fiber bundle 810 is schematically represented by lines 831-834. Optical fiber lines 831 to 834 end at the output port 840. It is observed here that, in one embodiment, the construction and operation of the fiber bundle 810 may be similar to that of the fiber bundle 740 in FIG. 7. Motorized switching mechanism 820 selectively positions the output from one of the optical fiber lines 831-834 to input slit port 860 of spectrometer 870 such that the optical dataset from a selected region of the sample is communicated to the spectrometer. Optical information processed by spectrometer 870 is directed to CCD 880. In one embodiment, CCD 880 can produce an image of the selected region of the sample as communicated by the optical fiber lines 831-834. In an alternative embodiment, CCD 880 can display an image of the single zone (not shown) or compile the images from optical fiber lines 831-834 and display an omnibus image (not shown) depicting an entire field of view for the sample (not shown). It may take approximately 1 second to capture optical dataset for the image of the corresponding FOV from a linear fiber array slit, thereby providing a quick imaging of the desired FOV.

In one embodiment, the translational movement of the motorized linear stage 820 may be controlled by a computer, controller, or a programmed processor (e.g., the control unit 570 in the embodiment of FIG. 5). The motorized linear stage 820 may have a high position tolerance (less than 1 micron) for accurate alignment of a fiber "slit" with the spectrometer slit. Depending on the user-selected FOV, one or more zones of fibers may be selected by the controller for signal input (into the spectrometer). The controller may then control the movement of the motorized linear translating stage 820 so as to sequentially scan each linear fiber array providing the relevant portion of the optical dataset for the user-selected FOV. In one embodiment, the "central" fiber array (i.e., the fiber array corresponding to zone-1 in the illustration in FIG. 6) may constitute a "default" scanning position. In other words, the scanning of 1D fiber slits may start with the fiber slit corresponding to the central fiber array. The motorized stage may then scan (under control from a controller) the fiber slit corresponding to zone-2, and so on. Because there may be N numbers of linear fiber arrays (depending on the desired maximum size of the sample FOV), the user can switch from one FOV size to another at run-time, thereby activating the operation of the linear translating stage to gather signals from appropriate linear fiber arrays. In one embodiment, after zone-1 fibers are scanned and CCD data mapped into zone-1 image on a display screen (e.g., the display screen 580 in FIG. 5), the motorized linear translating stage 820 may position the fiber slit from zone-2 at the spectrometer input slit port 860. After CCD data collection of the optical data from zone-2 fibers, an image reconstruction software may be used to map the image data from the zone-2 fibers in appropriate peripheral locations (pixels) around the zone-1 image on the display screen, so as to obtain a 2D image format that corresponds to the zone-based 2D input fiber layout (e.g., as illustrated in FIG. 6) that is used to image a desired FOV. This approach may be repeated (with fibers from zone-3, zone-4, etc.) if a still larger FOV is desired.

The "breaking up" of the FOV (to be imaged) into different zones, using zone-specific fiber bundles to capture optical data from the corresponding portion of the FOV, followed by a sequential scanning (using a single spectrometer slit aligned with one fiber slit at a time) of each "linearized" or 1D fiber slit may allow for a large/flexible FOV without requiring an increase in the CCD size because the CCD processes optical data from only one zone of fibers at a time.

It is noted here that the spatial resolution of a FOV may be reciprocally proportional to the optical magnification selected by a user for viewing the image of the FOV. Similarly, the area of a FOV on sample may be also reciprocally proportional to the selected magnification. However, the area of the FOV is directly proportional to the total number of fiber zones. In one embodiment, a 532 nm excitation laser may be used to image the desired FOV of a sample in the range of approximately 538 to 650 nm wavelengths. The spectral resolution may be approximately 0.1 nm. As noted before, the shape of the imaged FOV (rectangular, square, circular, hexagonal, etc.) may depend on the shape of the 2D fiber zones.

Figure 9:
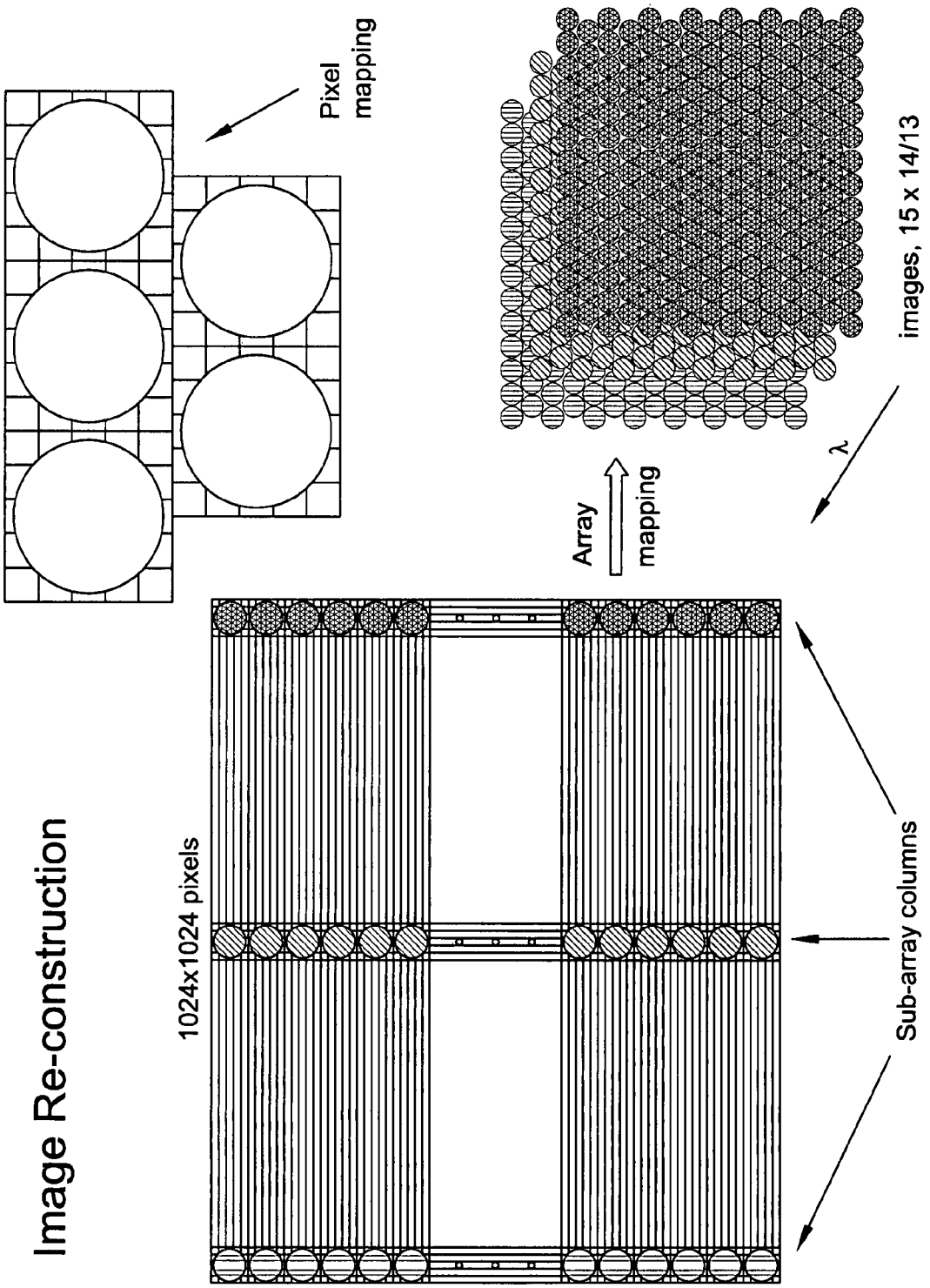
FIG. 9 is a schematic representation of image reconstruction according to one embodiment of the present disclosure at an exemplary CCD.

FIG. 9 is a schematic representation of image reconstruction according to one embodiment of the present disclosure at an exemplary CCD. In FIG. 9, an exemplary CCD with an array of 1024×1024 pixels is shown. The 1D output from a fiber "slit" may be fed to the spectrometer gratings (or other similar dispersive elements) through the spectrometer slit as illustrated in exemplary FIGS. 7 and 8. Each wavelength-dispersed signal (1D) from the gratings is sent to the CCD as illustrated in FIG. 8. In the embodiment of FIG. 9, each column of CCD pixels may represent one wavelength. In an exemplary illustration of pixel mapping in FIG. 9, it is seen that 5 CCD pixels may be mapped to an image point (e.g., an optical fiber in the fiber slit at issue) at a particular wavelength. Thus, in case of 1024 pixels in a CCD column, approximately 204 to 205 (1024 divided by 5) image points (or linear fiber array outputs in a fiber slit) can be accommodated for imaging the corresponding FOV at a particular wavelength. The entire CCD in the embodiment of FIG. 9 can then accommodate approximately 204 to 205 different columns of wavelengths (1024 pixels in a row divided by 5 pixels per column representing a wavelength) from a given fiber slit. A 1D-to-2D array mapping may then organize each column of CCD (containing optical data at a particular wavelength) back to or close to the layout of the corresponding original 2D fiber zone, so as to obtain a 2D spatially-accurate wavelength-resolved image (SAWRI) of the sample for the specific wavelength. In the exemplary illustration in FIG. 9, for the outputs from zone-1 fibers (FIG. 6), the array mapped image may have image pixels laid out in 15×14 or 15×13 format similar to that illustrated in the arrangement in FIG. 4. If desired, all wavelength-specific images may be combined to obtain a 3D spectral image of the FOV corresponding to a single zone of fibers. The 1D-to-2D array mapping process may be repeated for each selected zone of fibers to construct the SAWRI image of the entire user-selected FOV in substantial conformance with the input fiber zone layout in the exemplary FIG. 6 (e.g., by displaying image from zone-2 fibers on the periphery of the zone-1 image, image from zone-3 fibers on the periphery of the zone-2 image, and so on).

The above description is not intended and should not be construed to be limited to the examples given but should be granted the full breadth of protection afforded by the appended claims and equivalents thereto. Although the disclosure is described using illustrative embodiments provided herein, it should be understood that the principles of the disclosure are not limited thereto and may include modification thereto and permutations thereof.

I claim:

1. A system comprising: a first optical transmitter for converting a first 2D optical dataset collected from a first 2D portion of a sample to a first 1D optical dataset; a second optical transmitter for converting a second 2D optical dataset collected from a second 2D portion of the sample to a second 1D optical dataset; and a switching mechanism for selectively communicating one of the first 1D optical dataset or the second 1D optical dataset to a spectrometer.

2. The system of claim 1, further comprising said spectrometer coupled to said switching mechanism for receiving the first 1D optical dataset and the second 1D optical data set from said switching mechanism.

3. The system of claim 1, wherein the first 2D optical dataset and the second 2D optical dataset are non-overlapping.

4. The system of claim 1, wherein the first and the second 2D portions of said sample are non-overlapping.

5. The system of claim 1, wherein a combination of the first and the second 2D portions constitutes a field of view (FOV) of said sample.

6. The system of claim 1, wherein the first optical transmitter comprises a 2D array of M optical fibers at one end thereof and converted into a 1D curvilinear array of M optical fibers at the other end thereof, and wherein the second optical transmitter comprises a 2D array of N optical fibers at one end thereof and converted into a 1D curvilinear array of N optical fibers at the other end thereof.

7. The system of claim 6, wherein one of the following relationships exists: $M \leq N$; and $M \geq N$.

8. The system of claim 6, wherein the 2D array of M optical fibers in said first optical transmitter and the 2D array of N optical fibers in the second optical transmitter are stationary, and wherein said 1D array of M optical fibers in said first optical transmitter and the 1D array of N optical fibers in said second optical transmitter are non-stationary.

9. The system of claim 6, wherein said switching mechanism includes a motorized linear translating stage, and wherein said 1D array of M optical fibers and said 1D array of N optical fibers are attached to said translating stage.

10. The system of claim 9, wherein said spectrometer includes an input port and wherein said switching mechanism is configured to align one of said 1D array of M optical fibers or said 1D array of N optical fibers to said input port through sliding motion of said motorized linear translating stage.

11. The system of claim 1, wherein the switching mechanism facilitates communication of the first 1D optical dataset to the spectrometer independently of the second 1D optical dataset.

12. The system of claim 1, wherein the first 1D optical dataset and the second 1D optical dataset are generated in parallel.

13. The system of claim 12, wherein said switching mechanism is configured to sequentially communicate said first 1D optical dataset and said second 1D optical dataset to said spectrometer.

14. The system of claim 1, further comprising a third optical transmitter for converting a third 2D optical dataset to a third 1D optical dataset.

15. The system of claim 14, wherein the switching mechanism selectively communicates one of the first, second or third 1D optical datasets to the spectrometer.

16. The system of claim 1, wherein the spectrometer comprises a spectrograph.

17. The system of claim 1, wherein said spectrometer includes an output port, and wherein said system further comprises: an optical data collection unit coupled to said output port of said spectrometer to receive and store spectral data generated by said spectrometer from one of said first or said second 1D optical data sets.

18. The system of claim 17, wherein said optical data collection unit is a 2D CCD array.

19. The system of claim 18, further comprising: a processor coupled to said optical data collection unit to receive said spectral data therefrom and to convert said spectral data into a 2D spatially accurate wavelength resolved image (SAWRI) data of a corresponding one of said first or said second 2D portions of said sample; and a display unit coupled to said processor to receive said 2D SAWRI data therefrom and to responsively display a 2D SAWRI image of said corresponding one of said first or said second 2D portions of said sample.

20. The system of claim 19, wherein said optical data collection unit is configured to store a first spectral data generated by said spectrometer from said first 1D optical data set, wherein said processor is configured to generate a first 2D SAWRI data from said first spectral data, and wherein said display unit is configured to display a first 2D SAWRI image of said first 2D portion of said sample; and wherein said optical data collection unit is configured to store, after sending said first spectral data to said processor, a second spectral data generated by said spectrometer from said second 1D optical data set, wherein said processor is configured to generate a second 2D SAWRI data from said second spectral data, and wherein said display unit is configured to display a second 2D SAWRI image of said second 2D portion of said sample along with said first 2D SAWRI image.

21. The system of claim 19, wherein said 2D SAWRI image is one of the following: a 2D Raman image of a corresponding portion of said sample; a 2D luminescence image of a corresponding portion of said sample; and a 2D NIR image of a corresponding portion of said sample.

22. The system of claim 1, further comprising: an illumination source to illuminate said sample with an illumination wavelength; and an optical signal generation unit configured to receive light emitted, scattered, reflected, or transmitted by said sample upon illumination thereof.

23. The system of claim 22, wherein said illumination wavelength is selected from the group consisting of: visible wavelength range, UV wavelength range, NIR wavelength range.

24. The system of claim 22, wherein the optical signal generation unit is coupled to said first and said second optical transmitters.

25. The system of claim 22, wherein said optical signal generation unit includes an objective lens optically coupled to one of the following: a microlens array; and a combination of a mirror and a beam splitter.

26. A method comprising: converting a first 2D optical dataset depicting a first portion of a sample to a first 1D optical dataset; converting a second 2D optical dataset depicting a second portion of the sample to a second 1D optical dataset; and selectively communicating the first and the second 1D optical datasets to a spectrometer to obtain spectral data for the sample.

27. The method of claim 26, further comprising forming a spatially accurate wavelength resolved image of the sample.

28. The method of claim 26, wherein the step of selectively communicating further comprises: communicating the first 1D optical dataset to an input of the spectrometer, switching communication at the input of the spectrometer from the first 1D optical dataset to the second 1D optical dataset; and communicating the second 1D optical dataset to the spectrometer.

29. The method of claim 26, wherein the step of converting a first 2D optical dataset to a first 1D optical dataset further comprises: receiving said first 2D optical dataset from the first portion of the sample at an input of a first optical fiber bundle, and rearranging the first optical fiber bundle to convert the first 2D optical dataset from the first portion to the first 1D optical dataset at an output of the first optical fiber bundle.

30. The method of claim 26, wherein the step of converting a second 2D optical dataset to a second 1D optical dataset further comprises: receiving said second 2D optical dataset from the second portion of the sample at an input of a second optical fiber bundle, and rearranging the second optical fiber bundle to convert the second 2D optical dataset from the second portion to the second 1D optical dataset at an output of the second optical fiber bundle.

31. The method of claim 26, further comprising using M optical fibers for converting the first 2D optical dataset and using N optical fibers for converting the second 2D optical dataset, wherein $M \geq N$.

32. The method of claim 31 wherein the step of selectively communicating further comprises: sliding a motorized linear translating stage attached to said first optical fiber bundle of M optical fibers and said second optical fiber bundle of N optical fibers; and thereby aligning one of said 1D array of M optical fibers or said 1D array of N optical fibers to an input port of said spectrometer.

33. The method of claim 26, further comprising using M optical fibers for converting the first 2D optical dataset and using N optical fibers for converting the second 2D optical dataset, wherein M≦N.

34. The method of claim 26, wherein the spectrometer comprises a spectrograph.

35. The method of claim 26, further comprising: generating spectral data output from one of said first 1D optical dataset or said second 1D optical dataset; receiving with a 2D CCD array said spectral data output from an output port of said spectrometer storing said spectral data; processing said spectral data by converting the spectral data into a 2D spatially accurate wavelength resolved image (SAWRI) data of a corresponding one of said first or said second 2D portions of said sample; and displaying a 2D SAWRI image of said corresponding one of said first or said second 2D portions of said sample.

36. The method of claim 26, further comprising: illuminating said sample with an illumination wavelength; and receiving light emitted, scattered, reflected, or transmitted by said sample upon illumination thereof with an optical generation unit.

37. The method of claim 26, wherein the first portion and the second portion are non-overlapping.

38. The method of claim 26, further comprising converting a third 2D optical dataset from a third portion of the sample to a third 1D optical dataset and sequentially communicating each of the first, second and third 1D optical datasets to said spectrometer.

39. A system comprising:
a switching mechanism having
  an input for receiving a plurality of 1D optical datasets from a plurality of optical fiber bundles, wherein each optical fiber bundle converts a 2D optical dataset from a sample to a 1D optical dataset, and
  an output in optical communication with a spectrometer; and
a processor in communication with the switching mechanism and programmed with instructions for controlling the switching mechanism to:
select a first 1D optical dataset from one of the plurality of optical fiber bundles,
communicate the first 1D optical dataset to the spectrometer,
select a second 1D optical dataset from another of the plurality of optical fiber bundles, and
communicate the second optical 1D dataset to the spectrometer.

40. The system of claim 39, wherein the first 1D optical dataset is received from a first optical fiber bundle having M optical fibers and the second 1D optical dataset is received from a second optical fiber bundle having N optical fibers, wherein M≧N.

41. The system of claim 39, wherein the first 1D optical dataset is received from a first optical fiber bundle having M optical fibers and the second 1D optical dataset is received from a second optical fiber bundle having N optical fibers, wherein M≦N.

42. The system of claim 39, wherein the spectrometer is a spectrograph.

43. A system comprising: a switching mechanism having an input for receiving one of a plurality of optical fiber bundles, each one of the plurality of optical fiber bundles communicating a corresponding 1D optical dataset from a sample; and a processor in communication with the switching mechanism and programmed with instructions for controlling the switching mechanism to: select a first one of the plurality of optical fiber bundles to receive a first 1D optical dataset therefrom; communicate the first 1D optical dataset to a spectrometer; select a second one of the plurality of optical fiber bundles to receive a second 1D optical dataset therefrom; and communicate the second optical 1D dataset to the spectrometer.

44. The system of claim 43, wherein the switching mechanism further comprises an output in optical communication with the spectrometer.

45. The system of claim 43, wherein each optical fiber bundle converts a 2D optical dataset from a sample to a 1D optical dataset.

46. The system of claim 43, wherein the first optical fiber bundle comprises M optical fibers and the second optical fiber bundle comprises N optical fibers, wherein M≧N.

47. The system of claim 43, wherein the first optical fiber bundle comprises M optical fibers and the second optical fiber bundle comprises N optical fibers, wherein M≦N.

48. The system of claim 43, wherein the spectrometer is a spectrograph.

49. A fiber bundle comprising: an optical signal input end formed by a plurality of optical fibers organized in a plurality of non-overlapping 2D zones, wherein each zone includes a predetermined number of fibers; and an optical signal output end formed by a plurality of zone-specific curvilinear arrays of optical fibers in said plurality of optical fibers, wherein each curvilinear array contains a 1D arrangement of a corresponding set of zone-specific fibers from said plurality of fibers.

50. The fiber bundle of claim 49, wherein each of said plurality of zone-specific curvilinear array of optical fibers is configured to be optically coupled to a spectroscopy device.

51. The fiber bundle of claim 49, wherein said optical signal input end is configured to be optically coupled to an optical signal generation unit and said optical signal output end is configured to be optically coupled to a spectroscopy device.

* * * * *